(12) United States Patent
Tani et al.

(10) Patent No.: US 7,812,957 B2
(45) Date of Patent: *Oct. 12, 2010

(54) LIGHT MEASUREMENT APPARATUS MEASURING TWO-DIMENSIONAL PHYSICAL PROPERTIES OF A SAMPLE

(75) Inventors: Takeharu Tani, Kanagawa-ken (JP); Masayuki Naya, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/360,740

(22) Filed: Jan. 27, 2009

(65) Prior Publication Data

US 2009/0141283 A1    Jun. 4, 2009

Related U.S. Application Data

(63) Continuation of application No. 11/171,420, filed on Jul. 1, 2005, now Pat. No. 7,551,286.

(30) Foreign Application Priority Data

Jul. 5, 2004    (JP)    ............................. 2004-197667

(51) Int. Cl.
     *G01N 21/55*    (2006.01)
(52) U.S. Cl. .................................... 356/445
(58) Field of Classification Search ................. 356/445
     See application file for complete search history.

(56) References Cited

U.S. PATENT DOCUMENTS

2002/0126290 A1    9/2002   Naya
2002/0145737 A1    10/2002  Kubo et al.
2002/0154312 A1    10/2002  Ogura et al.

(Continued)

FOREIGN PATENT DOCUMENTS

JP    6-167443 A    6/1994

(Continued)

OTHER PUBLICATIONS

Takayuki Okamoto, "Surface Refracto-Sensor Using Evanscent Waves: Principles and Instrumentations", Spectrum Researches, vol. 47, No. 1, 1998, p. 19.

(Continued)

*Primary Examiner*—Tarifur Chowdhury
*Assistant Examiner*—Tara S Pajoohi
(74) *Attorney, Agent, or Firm*—Sughrue Mion, PLLC

(57) ABSTRACT

A measurement apparatus includes a dielectric block, a thin film layer formed on the dielectric block and brought into contact with a sample, a light source for generating a light beam, an optical incident system for causing the light beam to enter the dielectric block so that the light beam is totally reflected at the interface between the dielectric block and the thin film, and a two-dimensional light detection means for detecting the intensity of the light beam totally reflected at the interface. A predetermined pattern is formed within a region irradiated with the light beam on the dielectric block. The measurement apparatus includes a correction means for correcting an output from the two-dimensional light detection means, based on the pattern, so that an object on the face of the dielectric block is similar to the object detected by the two-dimensional detection means.

21 Claims, 10 Drawing Sheets

U.S. PATENT DOCUMENTS

2003/0179379 A1    9/2003    Gedig
2004/0061860 A1    4/2004    Naya

FOREIGN PATENT DOCUMENTS

| JP | 7-218222 A | 8/1995 |
|---|---|---|
| JP | 2001-45244 A | 2/2001 |
| JP | 2001-511249 | 8/2001 |
| JP | 2001-255267 A | 9/2001 |
| JP | 2002-286632 | 10/2002 |
| JP | 2002-357542 | 12/2002 |

OTHER PUBLICATIONS

Danny Van Noort, et al., "Porous Gold in Surface Plasmon Resonance Measurement" Eurosensors XIII, The 13$^{th}$ European Conference on Solid-State Transducers, Sep. 12-15, 1999, pp. 585-588.

P. I. Nikitin, et al., "Surface Plasmon Resonance Interferometry for Micro-Array Biosensing", Eurosensors XIII, The 13$^{th}$ European Conference on Solid-State Transducers, Sep. 12-15, 1999, pp. 235-238.

LIGHT MEASUREMENT APPARATUS MEASURING TWO-DIMENSIONAL PHYSICAL PROPERTIES OF A SAMPLE This is a continuation of application Ser. No. 11/171,420 filed Jul. 1, 2005 which claims priority from Japanese Patent Application No. 2004-197667 filed Jul. 5, 2004. The entire disclosures of the prior applications, are considered part of the disclosure of the accompanying divisional application and are hereby incorporated by reference.

BACKGROUND OF THE INVENTION

1. Field of the Invention

The present invention relates to a measurement apparatus, such as a surface plasmon resonance measurement apparatus, for obtaining the physical properties of a sample by utilizing generation of surface plasmons.

2. Description of the Related Art

Free electrons collectively oscillate in metal, and compressional waves called plasma waves are generated. When the compressional waves generated on the surface of the metal are quantized, they are called surface plasmons.

Conventionally, various surface plasmon resonance measurement apparatuses have been proposed for carrying out quantitative analyses on a substance in a sample, by utilizing a phenomenon where the surface plasmons are excited by a light wave. Among the surface plasmon resonance measurement apparatuses, an apparatus using a system called the Kretschmann configuration is well known (as disclosed in, for example, Japanese Unexamined Patent Publication No. 6 (1994)-167443).

A surface plasmon resonance measurement apparatus using the above-mentioned system basically includes a dielectric block which is, for example, prism-shaped, a metal film which is formed on a face of the dielectric block and brought into contact with a sample, and which has a refractive index lower than that of the dielectric block, and a light source for generating a light beam. The surface plasmon resonance measurement apparatus also includes an incident optical system for causing the light beam to enter the dielectric block at an angle which satisfies total reflection conditions at the interface between the dielectric block and the metal film. The surface plasmon resonance measurement apparatus also includes a light detection means for detecting a surface plasmon resonance state, namely an attenuated total reflection state, by measuring the intensity of the light beam which is totally reflected at the interface.

A relatively thin light beam may be deflected and caused to enter the interface so that the light beam enters the interface at various incident angles as described above. Alternatively, a relatively thick light beam in a convergent state or divergent state may be caused to enter the interface so that the light beam includes components that enter the interface at various angles. In the former case, as the light beam deflects, the reflection angle of the light beam changes. The light beam may be detected by a small light detector which moves synchronously with the deflection of the light beam. Alternatively, the light beam may be detected by an area sensor which extends along the direction of a change in the reflection angles. Meanwhile, in the latter case, light beams may be detected by an area sensor which extends in a direction so that it can detect each of all the light beams reflected at various reflection angles.

In the surface plasmon resonance measurement apparatus configured as described above, when a light beam is caused to enter the metal film at a specific incident angle $\theta_{sp}$ which is larger than or equal to a total reflection angle, an evanescent wave is generated. The electric field of the evanescent wave is distributed in the sample which is in contact with the metal film. Then, surface plasmons are excited at the interface between the metal film and the sample by the evanescent wave. When wave number matching is achieved as the wave number vector of the evanescent light is equal to the wave number of the surface plasmon, the evanescent light and the surface plasmon resonate. Then, light energy is transferred into surface plasmons. Therefore, the intensity of the light which is totally reflected at the interface between the dielectric block and the metal film sharply drops as illustrated in FIG. 3. Generally, the drop in the intensity of the light is detected as a dark line by the light detection means.

The resonance as described above only occurs when the incident beam is p-polarized. Therefore, it is required to set the surface plasmon resonance measurement apparatus in advance so that the light beam enters the interface in p polarization.

If the wave number of the surface plasmon is obtained based on an incident angle $\theta_{sp}$ when attenuated total reflection (ATR) occurs, the dielectric constant of the sample can be obtained. Specifically, if the wave number of the surface plasmon is $K_{sp}$, an angular frequency of the surface plasmon is $\omega$, the speed of light in a vacuum is c, and the dielectric constants of the metal and the sample are $\in_m$ and $\in_s$, respectively, the following relationship is satisfied:

$$k_{sp}(\omega) = \frac{\omega}{c}\sqrt{\frac{\varepsilon_m(\omega)\varepsilon_s}{\varepsilon_m(\omega) + \varepsilon_s}}$$

If the dielectric constant $\in_s$ of the sample is known, the density of a specific substance in the sample can be obtained based on a predetermined calibration curve or the like. Consequently, an incident angle $\theta$sp when the intensity of the reflected light drops can be obtained. Accordingly, the dielectric constant of the sample can be obtained. Consequently, the refractive index of the sample and the physical properties corresponding to the refractive index can be obtained.

Further, when a sensing material which specifically binds to a specific substance in the sample is fixed onto the metal film, if the specific substance is contained in the sample provided on the metal film, the specific substance binds to the sensing material. Accordingly, the refractive index of the sensing material changes. Therefore, the specific substance can be detected by detecting a change in the refractive index.

Further, a leaky mode measurement apparatus described, for example, in "Surface Refracto-sensor using Evanescent Waves: Principles and Instrumentations", by Takayuki Okamoto, Spectrum Researches, vol. 47, No. 1, 1998, pp. 21 through 23, 26 and 27 is also known as a similar measurement apparatuses utilizing the attenuated total reflection (ATR). The leaky mode measurement apparatus basically includes a dielectric block which is, for example, prism-shaped, a clad layer formed on a face of the dielectric block, and an optical waveguide layer which is formed on the clad layer and brought into contact with the sample. The leaky mode measurement apparatus also includes a light source for generating a light beam and an optical system for causing the light beam to enter the dielectric block at various angles so that total reflection conditions are satisfied at the interface between the dielectric block and the clad layer, and attenuated total reflection occurs due to excitation of a waveguide mode in the optical waveguide layer. The leaky mode measurement apparatus also includes a light detection means for detecting an excitation state of the waveguide mode by measuring the intensity of the light beam which has been totally reflected at the interface. The excitation state of the waveguide mode is an attenuated total reflection state.

In the leaky mode measurement apparatus configured as described above, when the light beam is caused to enter the clad layer through the dielectric block at an incident angle which is larger than or equal to a total reflection angle, the light beam is transmitted through the clad layer. After the light beam is transmitted through the clad layer, only light which has a specific wave number, and which has entered at a specific incident angle, propagates in a waveguide mode in the optical waveguide layer. When the waveguide mode is excited as described above, most of the incident light is absorbed in the optical waveguide layer. Accordingly, attenuated total reflection, in which the intensity of light totally reflected at the interface sharply drops, occurs. The wave number of the waveguide light depends on the refractive index of the sample on the optical waveguide layer. Therefore, if the specific incident angle when the attenuated total reflection occurs is obtained, the refractive index of the sample and the properties of the sample, which are related to the refractive index, can be measured.

There are various kinds of methods for analyzing samples by measuring the intensity of the light beam totally reflected at the interface using a light detection means. The samples may be analyzed as disclosed in "Porous Gold in Surface Plasmon Resonance Measurement", by D. V. Noort, et al., EUROSENSORS XIII, 1999, pp. 585-588. In this method, light beams which have a plurality of wavelengths are caused to enter the interface at incident angles which can satisfy total reflection conditions. Then, the intensity of the light beams which are totally reflected at the interface is measured for each of the wavelengths, and the degree of attenuated total reflection is detected for each of the wavelengths.

Alternatively, the samples may be analyzed as disclosed in "Surface Plasmon Resonance Interferometry for Micro-Array Biosensing", by P. I. Nikitin, et al., EUROSENSORS XIII, 1999, pp. 235-238. In this method, the light beams are caused to enter the interface so that total reflection conditions are satisfied. At the same time, a part of the light beams is separated into a spectrum before they enter the interface, and the spectral light beams are caused to interfere with the light beams which were totally reflected at the interface. Then, the intensity of the light beams after interference may be detected to analyze the samples.

When the physical properties of samples are analyzed, there are cases in which a plurality of samples is required to be measured under the same conditions. There are also cases in which information about the two-dimensional physical properties of the samples is required to be obtained. The surface plasmon resonance measurement apparatus and the leaky mode measurement apparatus, as described above, may be also applied to these cases (please refer to Japanese Unexamined Patent Publication No. 2001-255267 and Japanese Unexamined Patent Publication No. 2001-511249, for example). A case of applying the surface plasmon resonance measurement apparatus will be described as an example. The relationship illustrated in FIG. 3 changes in the direction of the horizontal axis of FIG. 3 as the refractive index of a substance which is present on the metal film changes. Therefore, when a light beam is caused to enter a region which two-dimensionally spreads on the interface, at a predetermined incident angle, if a light component enters a part of the region, which has a refractive index as attenuated total reflection occurs when the light beam enters at the incident angle, the light component is detected as a dark line. Specifically, the part of the region is a region at which a specific substance is present on the metal film. Therefore, if parallel light which has a relatively wide cross-section of beams is used, and the distribution of the intensities of light on the cross-section of the light beams totally reflected at the interface is detected, the distribution of the specific substance within a plane along the interface can be measured. Further, as illustrated in FIG. 3, the intensity of the totally reflected light becomes lower around the predetermined incident angle $\theta_{sp}$. Therefore, the distribution of the intensities of light on the cross-section of the light beams which entered the interface at a predetermined incident angle, and which were totally reflected at the interface, shows two-dimensional distribution of the refractive indices of the substance (sample) which is present on the metal film.

When the leaky mode measurement apparatus is used, the attenuated total reflection occurs because of excitation of the waveguide mode in the waveguide layer instead of the surface plasmon resonance. However, other features are the same as the surface plasmon resonance measurement apparatus. Therefore, even if the leaky mode measurement apparatus is used, it is possible to obtain the two-dimensional physical properties of the sample in the same manner as the surface plasmon resonance measurement apparatus.

In the specification of the present application, the phrase "to obtain the two-dimensional physical properties of the sample" refers to obtainment of the two-dimensional physical properties of a single sample. The phrase also refers to obtainment of the physical properties of a plurality of the same kind of samples or various types of samples, which is two-dimensionally arranged on a thin film layer, so that the physical properties of each of the plurality of samples are obtained independently from each other.

In the surface plasmon resonance measurement apparatus and the leaky mode measurement apparatus as described above, the light beams are caused to be totally reflected at the interface between the dielectric block and the thin film layer (the thin film layer is the metal film in the former case, and it is the clad layer and optical waveguide layer in the latter case). Accordingly, evanescent waves which are generated in the total reflection state and the surface plasmon or the waveguide mode are coupled with each other. A similar surface plasmon resonance measurement apparatus and leaky mode measurement apparatus may be configured by forming a diffraction grating on a face of the dielectric block instead of causing the light beams to be totally reflected at the face of the dielectric block. Specifically, in that case, if the light beam is caused to enter the diffraction grating from the side of the dielectric block, evanescent light is generated by diffraction. The evanescent light penetrates into the thin film layer, and is coupled with the surface plasmon or the waveguide mode. Therefore, the intensity of light which is reflectively diffracted toward the dielectric block attenuates. Hence, the refractive index of the sample and the physical properties of the sample, related to the refractive index, can be analyzed by obtaining the incident angle of the light beam which enters the diffraction grating when the intensity of light attenuates.

Further, the surface plasmon resonance measurement apparatus and the leaky mode measurement apparatus as described above are used to analyze samples by utilizing a characteristic that an incident angle $\theta$ of the light beam, when totally reflected light or reflectively diffracted light attenuates, changes according to the refractive index of the sample. However, the samples may be analyzed in a similar manner even if the incident angle $\theta$ is constant. Specifically, if the incident angle $\theta$ of the light beam is constant, totally reflected light or reflectively diffracted light attenuates when the wavelength λ of the light beam is a specific value $\lambda_{sp}$, as illustrated in FIG. 4. The specific value $\lambda_{sp}$ of the wavelength, when the totally reflected light or the reflectively diffracted light attenuates, is determined by the refractive index of the sample. Therefore, if the specific value $\lambda_{sp}$ of the wavelength is detected, the refractive index of the sample and the physical properties of the sample, related to the refractive index, can be analyzed.

The measurement apparatus as described above is particularly advantageous to obtain the two-dimensional physical properties of the sample. Specifically, when the two-dimensional physical properties of the sample are obtained, a light source which generates light beams, such as white light having a certain range of wavelengths, is used. Further, a two-dimensional light detection means for spectrally detecting the totally reflected light or the reflectively diffracted light is used. Since it is not required to change the incident angle of the light beam which enters the interface or the diffraction grating, a predetermined position of the sample can be stably irradiated.

In the surface plasmon resonance measurement apparatus and the leaky mode measurement apparatus as described above, a two-dimensional image detected by the two-dimensional light detection means may be distorted. The aspect ratio of the two-dimensional image may be different from that of an image produced on an actual measurement plane. Specifically, the actual measurement plane is a face of the dielectric block, on which a thin film layer (the thin film layer is a metal film in the case of the surface plasmon resonance measurement apparatus, and it is a clad layer and an optical waveguide layer in the case of the leaky mode measurement apparatus) or a diffraction grating is formed. The image is distorted because the light beam is refracted at a light emission plane of the prism-shaped dielectric block. The image is also distorted because the measurement plane is inclined with respect to the axis of the light beam.

A method for correcting a detected image by an operation based on already-known information about the distortion of the two-dimensional image detected by the two-dimensional light detection means is disclosed in Japanese Unexamined Patent Publication No. 2001-255267. In this method, the detected image is corrected so that the aspect ratio of the detected image becomes the same as that of the measurement plane. The aspect ratio of the image can be restored by using this method. However, it is impossible to recognize at which part of the measurement plane the sample is measured. Therefore, when two-dimensional physical properties of a single sample are obtained as described above, there is a problem that the two-dimensional distribution of the physical properties is erroneously obtained. Further, when the property of each of a plurality of samples which are two-dimensionally arranged on the measurement plane is obtained, there is a problem that the physical property of a certain sample is erroneously obtained as that of a different sample.

SUMMARY OF THE INVENTION

In view of the foregoing circumstances, it is an aspect of the present invention to accurately recognize at which part of the measurement plane a sample is measured when the sample is measured by a surface plasmon resonance measurement apparatus or a leaky mode measurement apparatus for measuring the two-dimensional physical properties of the sample.

A first measurement apparatus according to the present invention is configured under the premise that the physical properties of a sample are measured by utilizing attenuation of totally reflected light as described above. Specifically, the first measurement apparatus according to the present invention is a measurement apparatus comprising:

a dielectric block;

a thin film layer which is formed on a face of the dielectric block and brought into contact with a sample, and which has a refractive index lower than that of the dielectric block;

a light source for generating a light beam;

an incident optical system for causing the light beam to enter the dielectric block so that total reflection conditions are satisfied at the interface between the dielectric block and the thin film layer;

a two-dimensional light detection means for measuring the intensity of the light beam totally reflected at the interface at each of a plurality of positions on the cross-section of the beam; and a correction means, wherein a predetermined pattern is formed within a region irradiated with the light beam on the face of the dielectric block, and wherein the correction means is a means for correcting an output from the two-dimensional light detection means, based on the pattern, so that the shape of an object on the face of the dielectric block and the shape of the object, detected by the two-dimensional light detection means, are similar to each other.

A second measurement apparatus according to the present invention is also configured under the premise that the physical properties of a sample are measured by utilizing the attenuation of totally reflected light. Specifically, the second measurement apparatus according to the present invention is a measurement apparatus comprising:

a dielectric block;

a thin film layer;

a light source;

an incident optical system; and a two-dimensional light detection means, wherein the dielectric block, thin film layer, light source, incident optical system, and two-dimensional light detection means are similar to those of the first measurement apparatus as described above. The second measurement apparatus is a measurement apparatus further comprising:

a display means;

an input means; and a correction means, wherein a predetermined pattern is formed within a region irradiated with the light beam on the face of the dielectric block, and wherein the display means is a means for displaying an image of the predetermined pattern detected by the two-dimensional light detection means, and wherein the input means is a means for inputting information representing a standard point in the pattern displayed on the display means, and wherein the correction means is a means for correcting an output from the two-dimensional light detection means, based on the input information about the standard point, so that a position on the face of the dielectric block corresponds to a position on a light detection surface of the two-dimensional light detection means.

Meanwhile, a third measurement apparatus according to the present invention is configured under the premise that the physical properties of a sample are measured by utilizing the attenuation of reflectively diffracted light as described above. Specifically, the third measurement apparatus according to the present invention is a measurement apparatus comprising:

a dielectric block;

a diffraction grating formed on a face of the dielectric block;

a thin film layer which is formed on the diffraction grating and brought into contact with a sample;

a light source for generating a light beam;

an incident optical system for causing the light beam to enter the dielectric block so that at least a part of the diffraction grating is irradiated;

a two-dimensional light detection means for measuring the intensity of the light beam which has been reflectively diffracted at the diffraction grating at each of a plurality of positions on the cross-section of the beam; and a correction means, wherein a predetermined pattern is formed within a region irradiated with the light beam on the face of the dielectric block, and wherein the correction means is a means for correcting an output from the two-dimensional light detection means, based on the pattern, so that the shape of an object on the face of the dielectric block and the shape of the object, detected by the two-dimensional light detection means, are similar to each other.

A fourth measurement apparatus according to the present invention is also configured under the premise that the physical properties of a sample are measured by utilizing the attenuation of reflectively diffracted light. Specifically, the fourth measurement apparatus according to the present invention is a measurement apparatus comprising:

a dielectric block;
a diffraction grating;
a thin film layer;
a light source;
an incident optical system; and
a two-dimensional light detection means, wherein the dielectric block, diffraction grating, thin film layer, light source, incident optical system, and two-dimensional light detection means are similar to those of the third measurement apparatus as described above. The fourth measurement apparatus is a measurement apparatus further comprising:

a display means;
an input means; and
a correction means, wherein a predetermined pattern is formed within a region irradiated with the light beam on the face of the dielectric block, and wherein the display means is a means for displaying an image of the predetermined pattern detected by the two-dimensional light detection means, and wherein the input means is a means for inputting information representing a standard point in the pattern displayed on the display means, and wherein the correction means is a means for correcting an output from the two-dimensional light detection means, based on the input information about the standard point, so that a position on the face of the dielectric block corresponds to a position on a light detection surface of the two-dimensional light detection means.

In each of the measurement apparatuses according to the present invention as described above, a pattern produced by forming the thin film layer into a predetermined pattern may be used as the predetermined pattern. Alternatively, a predetermined pattern may be produced by forming a material, such as a thin metal film, having a refractive index which is different from that of the sample, into the predetermined pattern. Further, the predetermined pattern made of the thin film layer, thin metal film, or the like may be a rectangular pattern. The predetermined pattern may be a cyclic pattern.

Further, the predetermined pattern may be formed by a concavity formed on a face of the dielectric block.

The concavity may be, for example, dot-shaped. In that case, it is preferable that the concavity is arranged at the position of each vertex of a rectangle, or that concavities are arranged cyclically.

The concavity as described above may be linearly shaped. In that case, it is preferable that a rectangular pattern is formed by the concavity, or that concavities are arranged cyclically.

Meanwhile, in the measurement apparatuses according to the present invention, it is preferable that the light source generates a light beam which has a certain range of wavelengths. Further, it is preferable that the two-dimensional light detection means is a means for spectrally detecting the light beam.

In the first and third measurement apparatuses according to the present invention, a thin film layer or a diffraction grating is formed on a face of a dielectric block, which is a measurement plane. A predetermined pattern is formed within a region irradiated with the light beam on the face of the dielectric block. The first and third measurement apparatuses also include a correction means for correcting an output from a two-dimensional light detection means, based on the pattern, so that the shape of an object on the face of the dielectric block and the shape of the object, detected by the two-dimensional light detection means, are similar to each other. Therefore, it is possible to accurately recognize which part of the measurement plane is measured by producing an image based on the corrected output from the two-dimensional light detection means.

In the second and fourth measurement apparatuses according to the present invention, a thin film layer or a diffraction grating is formed on a face of a dielectric block, which is a measurement plane. A predetermined pattern is formed within a region irradiated with the light beam on the face of the dielectric block. The second and fourth measurement apparatuses also include a display means for displaying an image of the predetermined pattern detected by the two-dimensional light detection means, an input means for inputting information representing a standard point in the pattern displayed on the display means, and a correction means for correcting an output from the two-dimensional detection means, based on the input information about the standard point, so that a position on the face of the dielectric block corresponds to a position on a light detection surface of the two-dimensional light detection means. Therefore, it is possible to accurately recognize which part of the measurement plane is measured by producing an image based on the corrected output from the two-dimensional light detection means.

DESCRIPTION OF THE PREFERRED EMBODIMENTS

Hereinafter, embodiments of the present invention will be described in detail with reference to the attached drawings.

Figure 1:
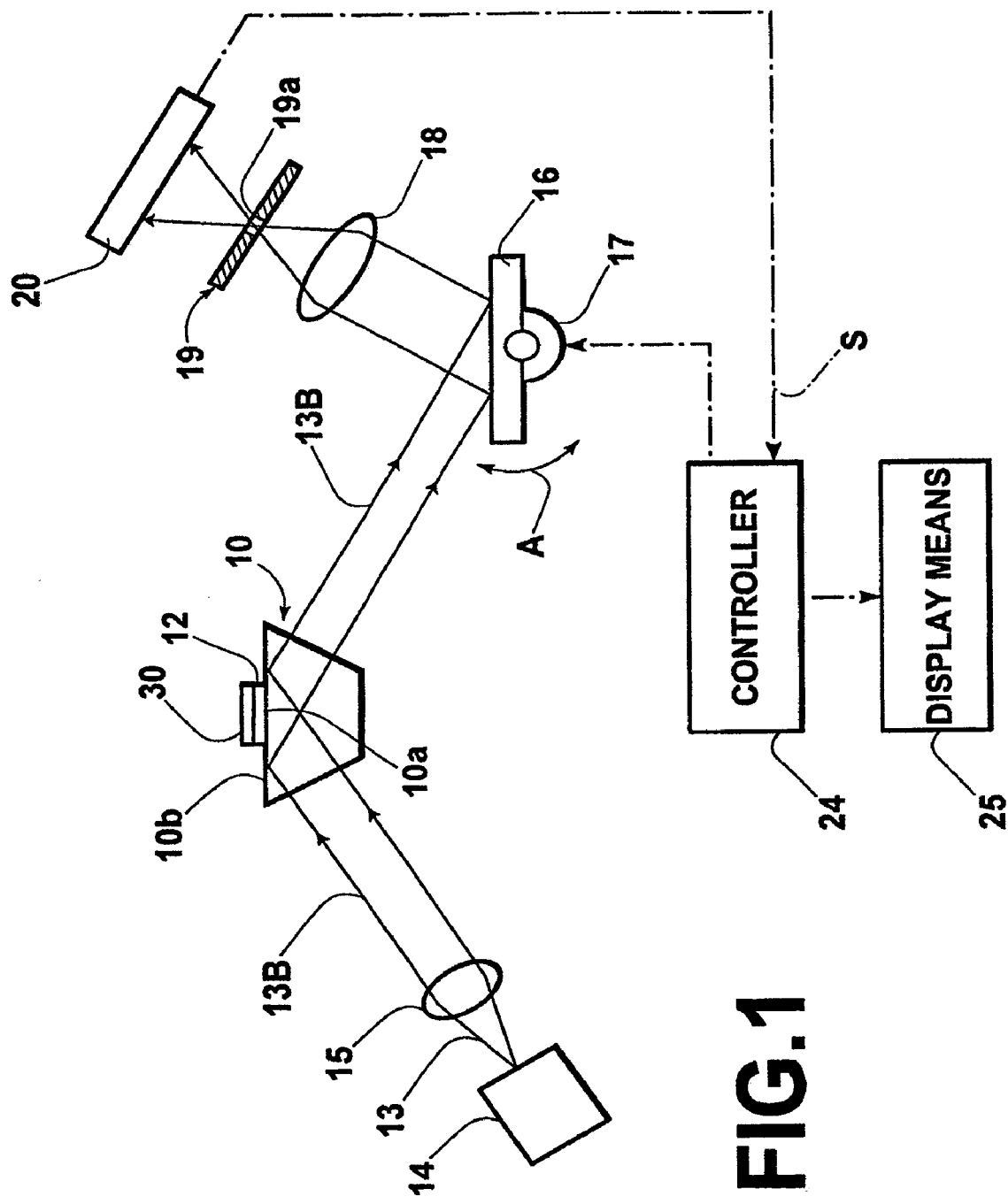
FIG. 1 is a schematic side view illustrating a surface plasmon resonance measurement apparatus according to a first embodiment of the present invention.

FIG. 1 illustrates a side view of a measurement apparatus according to a first embodiment of the present invention. The measurement apparatus according to the present embodiment is, for example, a surface plasmon resonance measurement apparatus as described above. The measurement apparatus includes a dielectric block 10 made of optical glass such as a transparent synthetic resin or BK7. The shape of the cross-section of the dielectric block 10 is substantially a trapezoid, for example. The measurement apparatus also includes a metal film 12 which is made of gold, silver, copper, aluminum, or the like, and which is formed on a face 10b (the upper side in FIG. 1) of the dielectric block 10. The measurement apparatus also includes a light source 14 which emits white light 13. The measurement apparatus also includes an incident optical system 15 for collimating the white light 13 which is emitted from the light source 14 in a divergent state. The incident optical system 15 further causes collimated light beams 13B to enter the dielectric block 10 so that the light beams 13B are directed to the metal film 12.

Further, the surface plasmon resonance measurement apparatus also includes a diffraction grating 16. The diffraction grating 16 is placed at a position so that the light beams 13B which were totally reflected at the interface 10a between the dielectric block 10 and the metal film 12 enter the diffraction grating 16. The surface plasmon resonance measurement apparatus also includes a diffraction grating drive means 17 which rotates the diffraction grating 16 in a direction (the direction of arrow A) so that the incident angle of the light beams 13B changes according to the rotation. The surface plasmon resonance measurement apparatus also includes a condensing lens 18 which causes the light beams 13B which were reflectively diffracted at the diffraction grating 16 to converge. The surface plasmon resonance measurement apparatus also includes a pinhole plate 19 which is placed at a position at which the light beams 13B converge when they are condensed by the condensing lens 18. The surface plasmon resonance measurement apparatus also includes a CCD (charge-coupled device) area sensor 20. The CCD area sensor 20 two-dimensionally detects the light beams 13B which have passed through a pinhole 19a of the pinhole plate 19.

An output signal from the CCD area sensor 20 is input to a controller 24 of the surface plasmon resonance measurement apparatus. Then, an analysis result by the controller 24, which will be described later, is displayed on a display means 25.

An incident angle θ of the light beam 13B which enters the interface 10a should be larger than or equal to a critical angle. The incident angle θ should be also within a range of angles as the surface plasmon is excited. The light beam 13B is totally reflected at the interface 10a. Further, the light beam 13B is caused to enter the interface 10a in p polarization. For that purpose, the direction of polarization of the white light 13 should be controlled by setting a wavelength plate or polarization plate in the light source 14.

Hereinafter, the operation of the surface plasmon resonance measurement apparatus configured as described above will be described. When samples are analyzed by the surface plasmon resonance measurement apparatus of the present invention, a sample 30 which is an analysis object is placed on the metal film 12. The light source 14 is turned on while the sample 30 is placed on the metal film 12. Then, the light beams 13B which are collimated white light enter the dielectric block 10. The light beams 13B are totally reflected at the interface 10a between the dielectric block 10 and the metal film 12. The light beams 13B are emitted from the dielectric block 10, and reflectively diffracted at the diffraction grating 16. Since the diffraction angle differs depending on the wavelength λ of the light beams 13B, the light beams 13B in a spatially spectral state are emitted from the diffraction grating 16.

The spectral light beams 13B are condensed by the condensing lens 18. The light beams 13B pass through the pinhole 19a of the pinhole plate 19 which is placed at a position at which the light beams 13B converge, and enter the CCD area sensor 20. The CCD area sensor 20 detects the intensity of the light beams 13B at each position on the cross-section of the beams. The CCD area sensor 20 inputs a light detection signal S which represents the detected intensity of the light to the controller 24 which includes a computer system, for example.

Since the light beams 13B which enter the pinhole plate 19 are spatially spectral light, as described above, light only in a certain narrow range of wavelengths passes through the pinhole 19a. When the samples are analyzed, the diffraction grating 16 is rotated as described above. Accordingly, the wavelengths of the light beams 13B which pass through the pinhole 19a are swept, and the CCD area sensor 20 detects the intensity of light for each of the wavelengths which are swept as described above.

Figure 4:
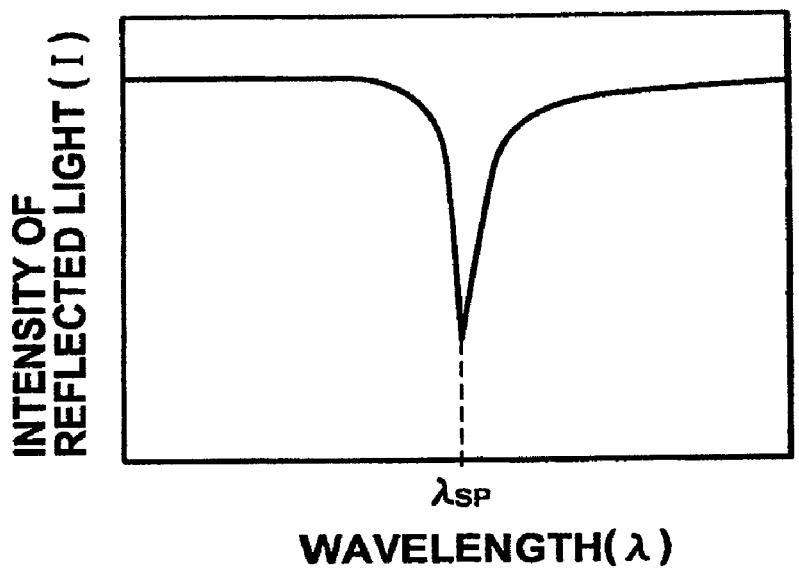
FIG. 4 is a graph showing a relationship between measured wavelengths of light and the detected intensities of light when a surface plasmon resonance measurement apparatus is used.

At this time, if a range of wavelengths to be swept is appropriately set, totally reflected light attenuates at a specific wavelength $\lambda_{sp}$ because of surface plasmon resonance, as described above with reference to FIG. 4. The attenuated total reflection is detected by the CCD area sensor 20 as a sharp drop in the detected intensity of light. Since the value of the specific wavelength $\lambda_{sp}$ uniquely corresponds to the refractive index of the sample 30. Therefore, the refractive index of the sample 30 and the physical properties of the sample 30, which correspond to the refractive index of the sample 30, can be obtained based on the value of the wavelength $\lambda_{sp}$ when the totally reflected light attenuates. Specifically, they can be obtained based on the rotation position of the diffraction grating 16 when the totally reflected light attenuates. Therefore, the controller 24 obtains the physical properties of the sample 30, such as the refractive index, based on the light detection signal S and the rotation position of the diffraction grating 16, which is controlled by the controller 24. The relationship between the rotation position of the diffraction grating 16 and the physical properties of the sample may be obtained in advance based on experiments and experience.

In the present embodiment, the light beam 13B two-dimensionally irradiates the metal film 12. Then, the intensity of the light beam 13B which has been totally reflected is detected at each position of the cross-section of the beam. Therefore, the controller 24 can obtain two-dimensional distribution of the physical properties, such as the refractive index, of the sample 30. Then, the display means 25 produces and displays an image based on the two-dimensional distribution of the physical properties of the sample 30, obtained by the controller 24 as described above. For example, the display means 25 displays an image within the region of the metal film 12 using various density values which reflect the physical property values, such as the refractive indices.

Figure 2A:
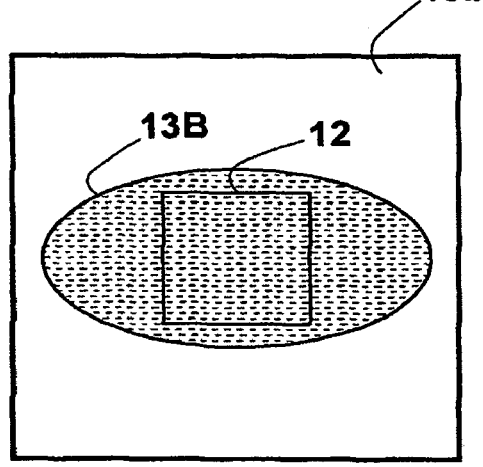
FIG. 2A is a schematic diagram illustrating the shape of a metal film on a measurement plane in the apparatus illustrated in FIG. 1.
Figure 2B:
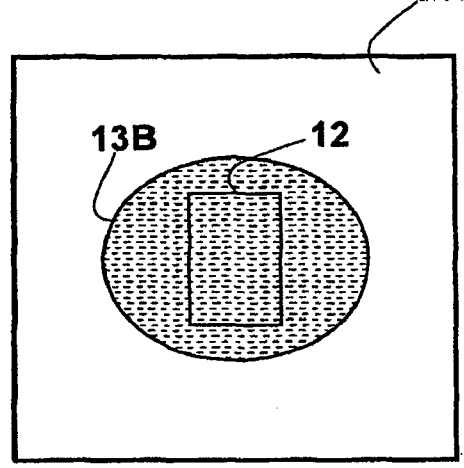
FIG. 2B is a schematic diagram illustrating the shape of an image of the metal film, detected by a light detection means.

Here, a plan view of the upper surface 10b of the dielectric block 10 is illustrated in FIG. 2A. Since the upper surface 10b of the dielectric block 10 is inclined with respect to the axis of the light beam 13B, the region irradiated with the light beam 13B on the upper surface 10b is oval as illustrated in FIG. 2A. Further, the light beam 13B enters the light detection surface 20a of the CCD area sensor 20 at a region of the light detection surface 20a as illustrated in FIG. 2B. The shape of the region of the light detection surface 20a, in which the light beam 13B enters, is not the same as that of the region irradiated with the light beam 13B on the upper surface 10b of the dielectric block. Therefore, when an image of the metal film 12 formed on the upper surface 10b of the dielectric block is detected at the light detection surface 20a, the detected image of the metal film 12 is distorted. Therefore, when an image is produced based on the physical property value such as the refractive index, and the produced image is displayed, there is a problem that the two-dimensional distribution of the physical property values is erroneously recognized. Further, when the physical property of each of a plurality of samples which are two-dimensionally arranged on the metal film 12 is obtained, there is a problem that the physical property of a sample is erroneously recognized as that of another sample.

Figure 2C:
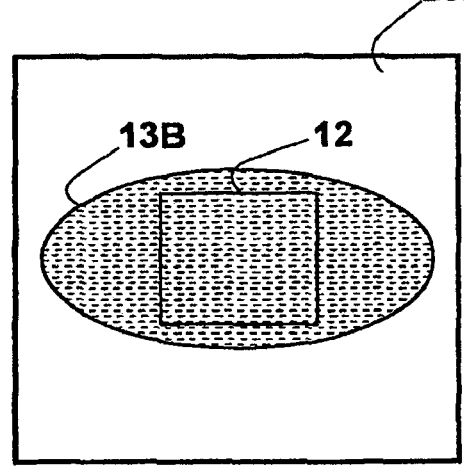
FIG. 2C is a schematic diagram illustrating the shape of a corrected image of the metal film.
Figure 3:
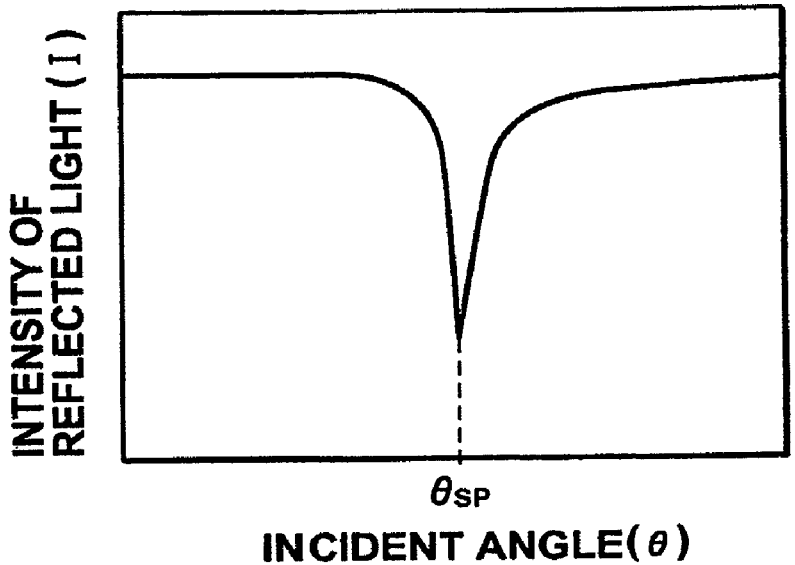
FIG. 3 is a graph showing a relationship between measured incident angles of light and detected intensities of light when a surface plasmon resonance measurement apparatus is used.

Hereinafter, the configuration of the measurement apparatus for preventing the problems as described above will be described. In the present embodiment, the metal film 12 has a predetermined rectangular pattern which can be placed within a region irradiated with the light beam 13B on the upper surface 10b of the dielectric block. The controller 24 including a computer system corrects the light detection signal S output from the two-dimensional light detection means. The controller 24 corrects the light detection signal S so that the shape of an object on the upper surface 10b of the dielectric block is similar to that of the object, detected by the CCD area sensor 20. Accordingly, the distribution of the physical property values is displayed on the display means 25 so that the physical property values are distributed within the region of the metal film 12, of which the shape is corrected as illustrated in FIG. 2C. The physical property values are distributed within the region of the metal film 12 of which the shape has been corrected. Since the distribution of the physical property values and positions on the metal film 12 correspond to each other, the problems as described above can be prevented.

Specifically, the light detection signal S is corrected as described below. First, a dielectric block 10 on which a metal film 12 similar to the one that will be used in actual analysis is prepared. Then, an undistorted image of the metal film 12 is obtained and input to the controller 24. The undistorted image is obtained, for example, by taking a photograph of a reflected image of the upper surface of the dielectric block 10 from a position directly above the metal film 12. The photograph is taken with a reference CCD area sensor which is the same as the CCD area sensor 20. The controller 24 detects a position at which the density value changes stepwise in the image of the metal film 12, input to the controller 24. Accordingly, the controller 24 obtains an outline image of the metal film 12. The controller 24 stores the outline image as a template. When a sample is actually analyzed, the controller 24 performs template matching by gradually inclining the template so that the template and an obtained outline image of the metal film 12 match each other. The controller 24 obtains the inclination of the image of the metal film 12, detected by the CCD area sensor 20, with respect to an actual image of the metal film 12. The controller 24 obtains the inclination based on the inclination of the template when the template and the obtained outline image match each other. Then, the controller 24 corrects the light detection signal S output from the two-dimensional light detection means so that the inclination of the image of the metal film 12, recognized as described above, is adjusted.

The method for correcting the light detection signal S output from the two-dimensional light detection means so that the shape of the object on the upper surface 10b of the dielectric block and that of the object, detected by the CCD area sensor 20, become similar to each other has been described. However, the method is not limited to the method as described above, and various other well-known methods for recognizing images can be applied to the present invention as appropriate.

Figure 5:
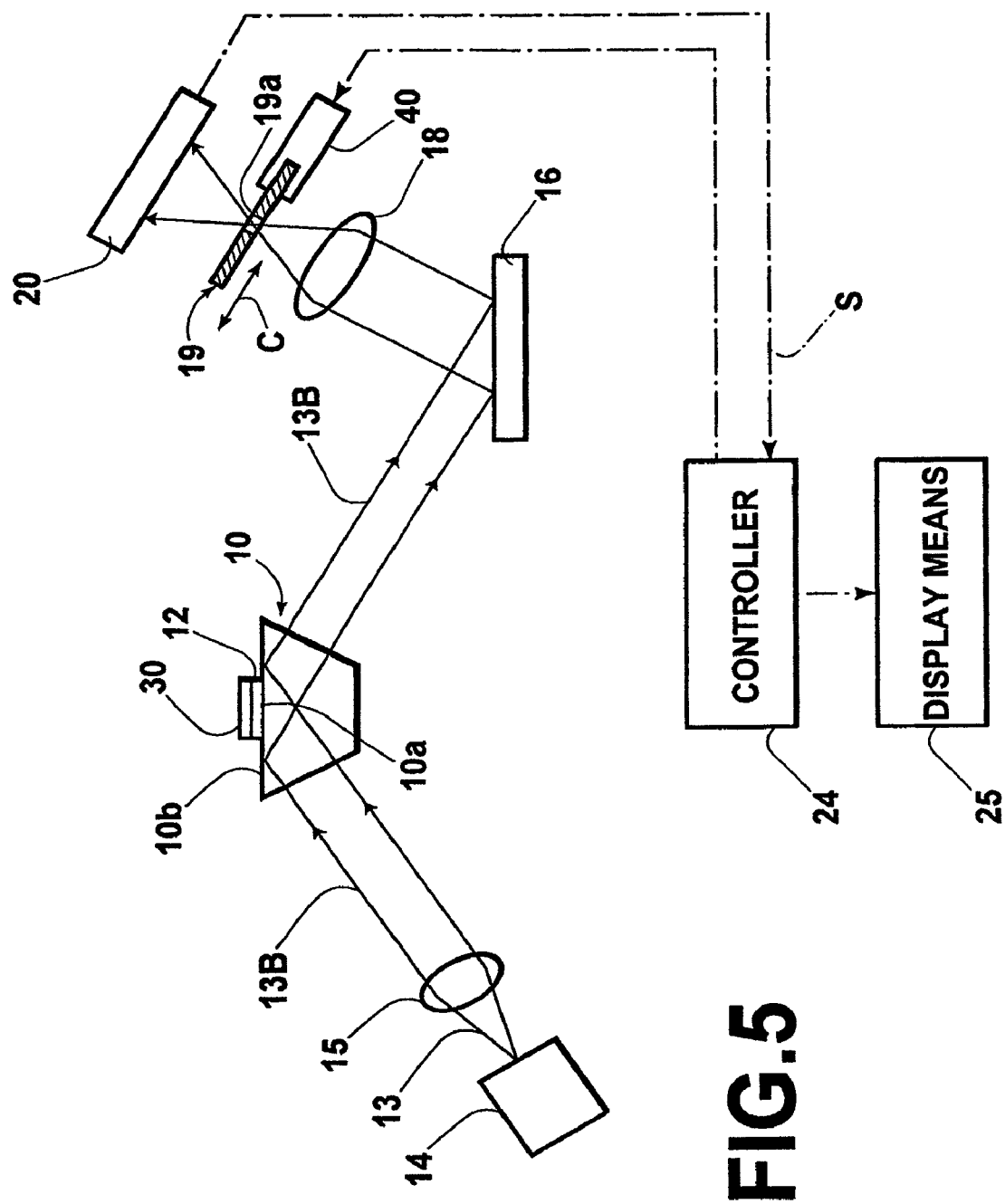
FIG. 5 is a schematic side view illustrating a surface plasmon resonance measurement apparatus according to a second embodiment of the present invention.

Next, a second embodiment of the present invention will be described. FIG. 5 is a side view of a measurement apparatus according to the second embodiment of the present invention. In FIG. 5, the same reference numerals are assigned to the elements equivalent to those of FIG. 1. Therefore, descriptions on the equivalent elements will be omitted unless such descriptions are particularly required (hereinafter, the same).

The apparatus according to the second embodiment of the present invention is also a surface plasmon resonance measurement apparatus, for example. However, the diffraction grating drive means 17 in the apparatus illustrated in FIG. 1 is omitted in the apparatus illustrated in FIG. 5. Instead, a pinhole plate drive means 40 for moving the pinhole plate 19 substantially toward the direction of the arrow C is provided in the apparatus in FIG. 5. The movement of the pinhole plate drive means 40 is controlled by the controller 24.

In the measurement apparatus of the present embodiment, the light detection signal is corrected by the controller 24 in the same manner as the first embodiment. Accordingly, a similar effect to that of the first embodiment can be achieved.

Figure 6:
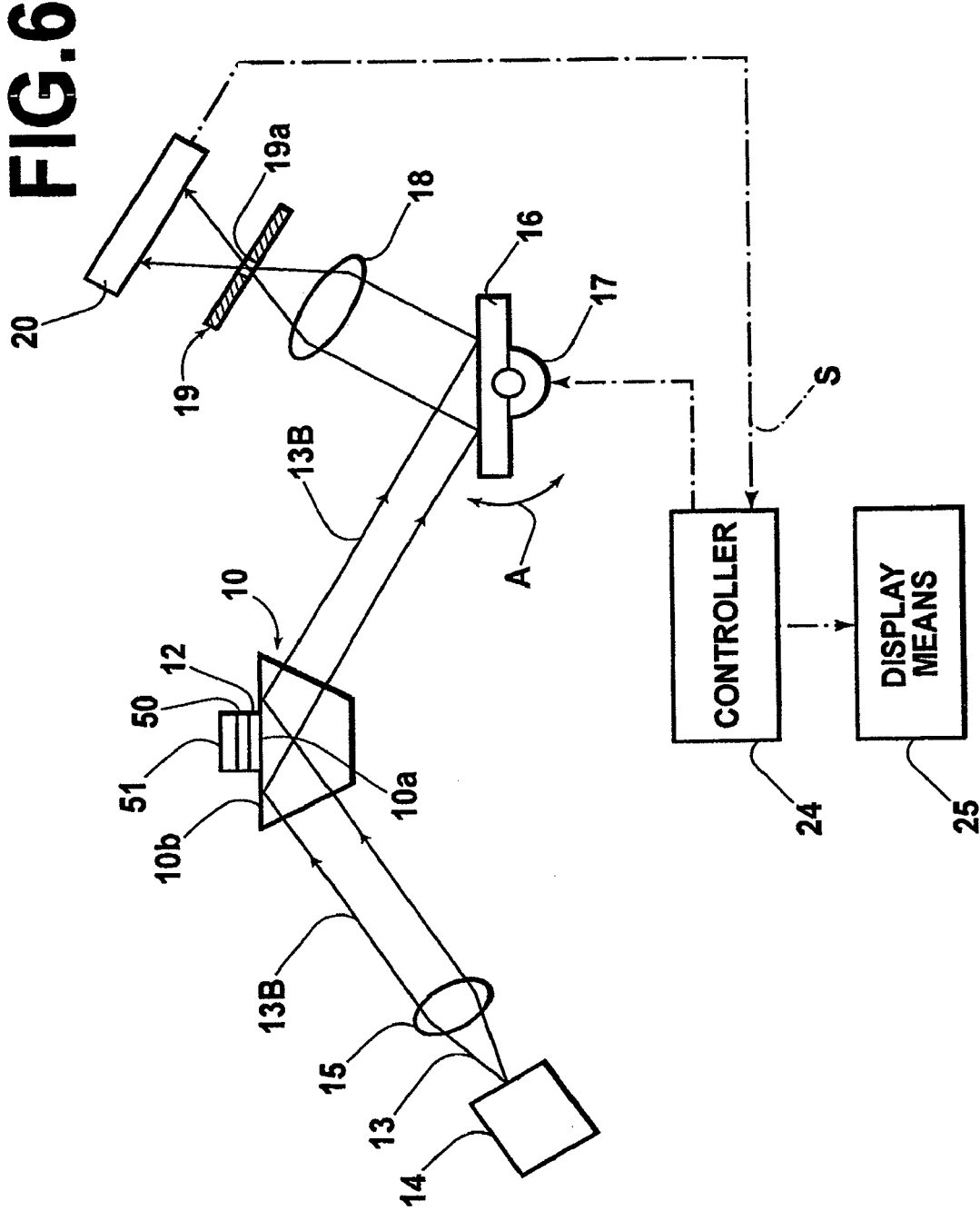
FIG. 6 is a schematic side view illustrating a surface plasmon resonance measurement apparatus according to a third embodiment of the present invention.

Next, a third embodiment of the present invention will be described. FIG. 6 is a side view of a measurement apparatus according to the third embodiment of the present invention. The apparatus according to the third embodiment is also a surface plasmon resonance measurement apparatus, for example. However, the measurement apparatus according to the third embodiment is different from the apparatus illustrated in FIG. 1 in that a sensing material 50 is fixed onto the metal film 12 in the apparatus of the third embodiment, illustrated in FIG. 6. The sensing material 50 is a material which specifically binds to a specific substance in a specimen 51 which will be described later.

When the specimen 51 is analyzed using the measurement apparatus configured as described above, the specimen 51 is placed on the sensing material 50. If the specific substance is contained in the specimen 51, the specific substance binds to the sensing material 50, and the refractive index of the sensing material 50 changes. Therefore, the wavelengths of the light beam 13B which enters the CCD area sensor 20 in a similar manner to the operations in the apparatus illustrated in FIG. 1 are swept both before and after the specimen 51 is placed on the sensing material 50. Consequently, it is detected whether the wavelength $\lambda_{sp}$ when the totally reflected light attenuates is different between before and after placement of the specimen 51 on the sensing material 50. Accordingly, it is possible to analyze whether the sensing material 50 has bound to the specific substance. Specifically, it is possible to analyze whether the specific substance is contained in the specimen 51.

In the measurement apparatus of the present embodiment, the light detection signal S is corrected by the controller 24 in the same manner as the first embodiment. Therefore, a similar effect to that of the first embodiment can be achieved.

The CCD area sensor 20 which measures the distribution of the intensities of light on the cross-section of the light beam 13B is used in the present embodiment. Therefore, it is possible to recognize at which part of the specimen 51 the sensing material 50 and the specific substance have bound to each other.

Further, a plurality of types of sensing materials may be fixed onto the metal film 12 at appropriate intervals instead of fixing a kind of sensing material 50 onto the metal film 12 as described above. If the plurality of types of sensing materials is fixed onto the metal film 12, it is possible to recognize, based on an output from the CCD area sensor 20, at which position of the metal film 12 the sensing material and the specific substance have bound to each other. Specifically, it is possible to recognize which kind of sensing material has bound to the specific substance.

Further, a plurality of a kind of sensing materials may be fixed onto the metal film 12 at appropriate intervals instead of fixing the plurality to types of sensing materials as described above. If a different specimen is provided for each of the sensing materials, it is possible to recognize, based on an output from the CCD area sensor 20, at which position of the metal film 12 the sensing material and the specific substance have bound to each other. Specifically, it is possible to recognize which specimen has bound to the sensing material.

The binding between the sensing material and the specific substance as described above is, for example, binding between various antibodies and antigens.

Figure 7:
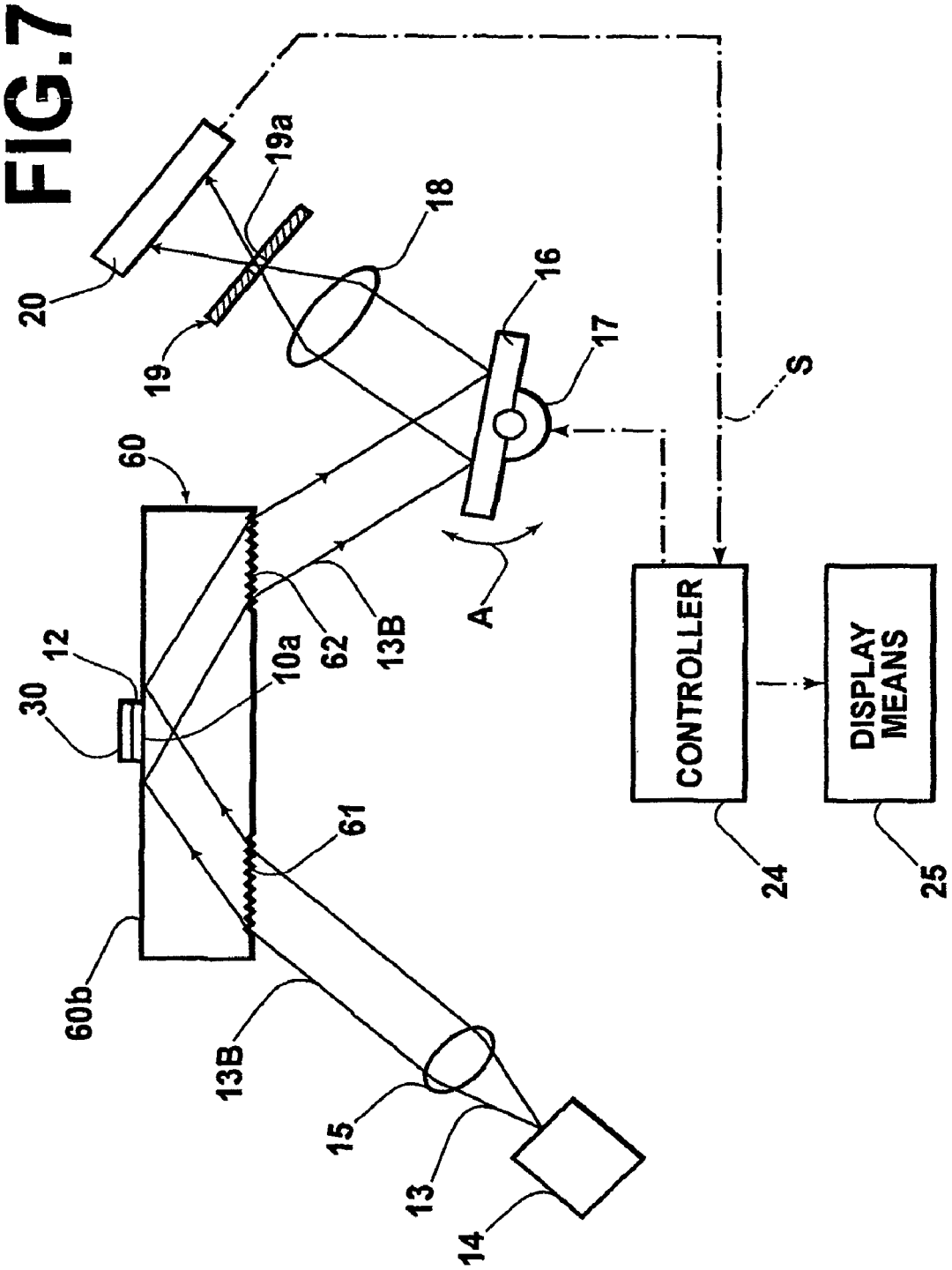
FIG. 7 is a schematic side view illustrating a surface plasmon resonance measurement apparatus according to a fourth embodiment of the present invention.

Next, a fourth embodiment of the present invention will be described. FIG. 7 illustrates a side view of a measurement apparatus according to the fourth embodiment of the present invention. The apparatus according to the fourth embodiment is also a surface plasmon resonance measurement apparatus, for example. However, FIG. 1 and FIG. 7 are different from each other in that a dielectric block 60 is used in the measurement apparatus of FIG. 7 instead of the dielectric block 10. The shape of the dielectric block 60 is a rectangular parallelepiped, and a diffraction grating 61 for light entering the dielectric block 60 and a diffraction grating 62 for light emitted from the dielectric block 60 are formed on the lower surface of the dielectric block 60.

In the measurement apparatus of the present embodiment, the light beam 13B is diffracted at the diffraction grating 61 for light entering the dielectric block 60. The diffracted light enters the interface 10a at an incident angle which can cause the light beam 13B to be totally reflected. After the light is totally reflected at the interface 10a, the light is diffracted at the diffraction grating 62 for light emitted from the dielectric block 60, and the diffracted light is emitted from the dielectric block 60. Other features of the measurement apparatus in the present embodiment are basically the same as those of the apparatus illustrated in FIG. 1.

In the measurement apparatus of the present embodiment, a metal film 12 which has a predetermined rectangular pattern is also placed within a region irradiated with the light beam 13B on an upper surface 60b of the dielectric block 60. The controller 24 corrects the light detection signal S in the same manner as the first embodiment. Therefore, a similar effect to that of the first embodiment can be achieved.

Figure 8:
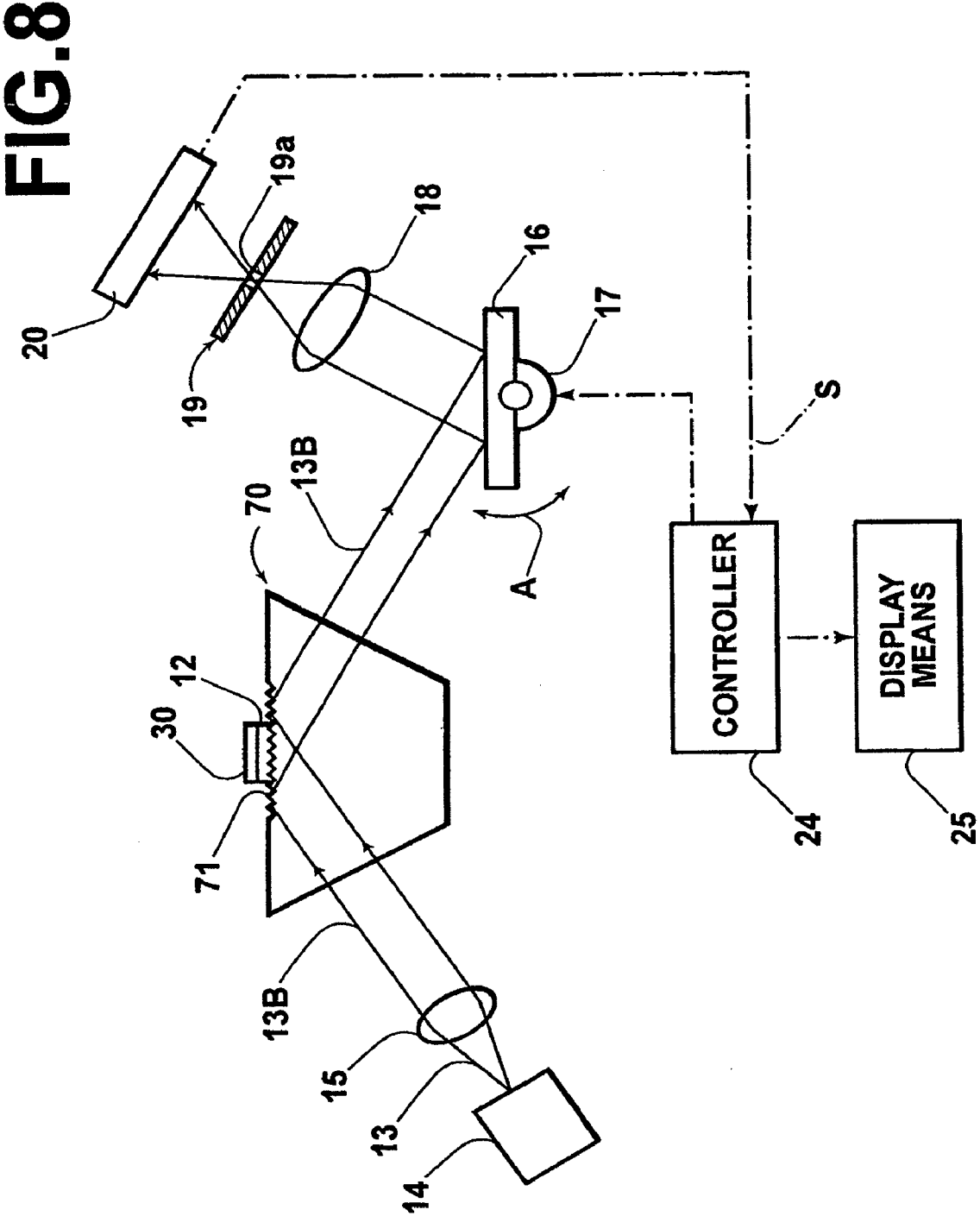
FIG. 8 is a schematic side view illustrating a surface plasmon resonance measurement apparatus according to a fifth embodiment of the present invention.

Next, a fifth embodiment of the present invention will be described. FIG. 8 illustrates a side view of a measurement apparatus according to the fifth embodiment of the present invention. The apparatus according to the fifth embodiment is also a surface plasmon resonance measurement apparatus, for example. The measurement apparatus according to the fifth embodiment and the measurement apparatus illustrated in FIG. 1 are different from each other in that a dielectric block 70 is provided in the measurement apparatus illustrated in FIG. 8 instead of the dielectric block 10 in the apparatus illustrated in FIG. 1. A diffraction grating 71 is formed on the upper surface (the surface on which the metal film is formed) of the dielectric block 70. The diffraction grating 71 is produced by forming uneven patterns on the upper surface of the dielectric block 70. A typical height and pitch of the uneven patterns is approximately several tens of nanometers (nm) and 1 µm, respectively.

In the measurement apparatus of the present embodiment, the light beam 13B is reflectively diffracted by the diffraction grating 71, and bounced. In this case, when the wavelength $\lambda$ of the light beam 13B is a specific value $\lambda_{sp}$, evanescent light which is generated by the diffraction, and which penetrates the metal film 12 interacts with the surface plasmon. Then, the intensity of the light beam 13B which is reflectively diffracted toward the dielectric block 70 sharply drops. Therefore, the refractive index of the sample 30 and the properties of the sample 30, which are related to the refractive index, can be analyzed by this apparatus in a similar manner to the apparatus illustrated in FIG. 1.

In the measurement apparatus of the present embodiment, a metal film 12 which has a predetermined rectangular pattern is also formed within the region irradiated with the light beam 13B on the diffraction grating 71. The controller 24 corrects the light detection signal S in the same manner as the first embodiment. Accordingly, a similar effect to that of the first embodiment can be achieved.

Figure 9:
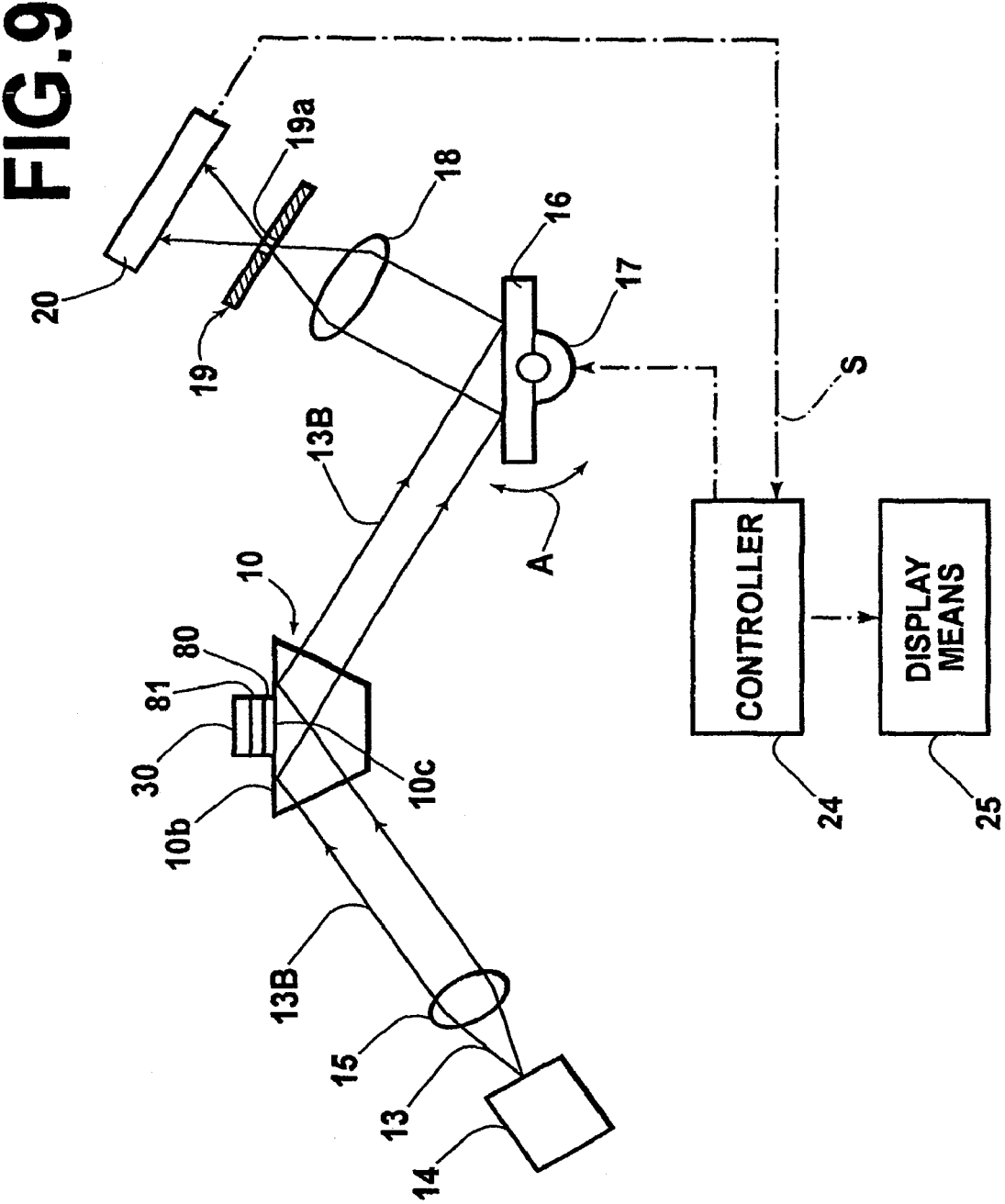
FIG. 9 is a schematic side view illustrating a leaky mode measurement apparatus according to a sixth embodiment of the present invention.

Next, a sixth embodiment of the present invention will be described. FIG. 9 illustrates a side view of a measurement apparatus according to the sixth embodiment of the present invention. The apparatus according to the sixth embodiment is a leaky mode measurement apparatus as described above. The leaky mode measurement apparatus in FIG. 9 and the measurement apparatus illustrated in FIG. 1 are different from each other in that a clad layer 80 and an optical waveguide layer 81 are provided in this order on the upper surface 10b of the dielectric block 10 of the apparatus illustrated in FIG. 9 instead of the metal film 12.

The dielectric block 10 is made of optical glass such as a transparent synthetic resin or BK7. The clad layer 80 is a thin film layer made of a dielectric material which has a refractive index lower than that of the dielectric block 10 or a metal such as gold. The optical waveguide layer 81 is also a thin film layer. The optical waveguide layer 81 is made of a dielectric material, such as PMMA (polymethylmethacrylate), which has a refractive index higher than that of the clad layer 80. The thickness of the clad layer 80 is 36.5 nm when the clad layer is, for example, made of a metal film. The thickness of the optical waveguide layer 81 is approximately 700 nm when the optical waveguide layer 81 is, for example, made of PMMA.

In the leaky mode measurement apparatus configured as described above, if the light beam 13B is caused to enter the clad layer 80 through the dielectric block 10 at an incident angle which is larger than or equal to a critical angle, the light beam 13B is totally reflected at the interface 10c between the dielectric block 10 and the clad layer 80. However, light which has a specific wavelength is transmitted through the clad layer 80 and enters the optical waveguide layer 81. Then, the light propagates through the optical waveguide layer 81 in a waveguide mode. When the waveguide mode is excited as described above, most of the incident light is absorbed in the optical waveguide layer 81. Therefore, the intensity of light totally reflected at the interface 10c sharply drops, and attenuated total reflection occurs.

The wave number of the waveguide light in the optical waveguide layer 81 depends on the refractive index of the sample 30 on the optical waveguide layer 81. Therefore, if the specific wavelength when the attenuated total reflection occurs is obtained within the range of swept wavelengths, the refractive index of the sample 30 and the physical properties of the sample 30, related to the refractive index, can be analyzed. Particularly, in the present embodiment, the intensity of the light beam 13B is detected by the CCD area sensor 20 at each position on the cross-section of the beam. Therefore, the controller 24 can obtain the two-dimensional distribution of the physical properties of the sample 30, such as the refractive index. The two-dimensional distribution of the physical properties of the sample 30, obtained by the controller 24 as described above, is displayed on the display means 25.

In the measurement apparatus of the present embodiment, the clad layer 80 and the optical waveguide layer 81 are produced so that they have a predetermined rectangular pattern within the region irradiated with the light beam 13B on the upper surface 10b of the dielectric block 10. The controller 24 corrects the light detection signal S in the same manner as the first embodiment. Therefore, a similar effect to that of the first embodiment can be achieved.

Figure 10:
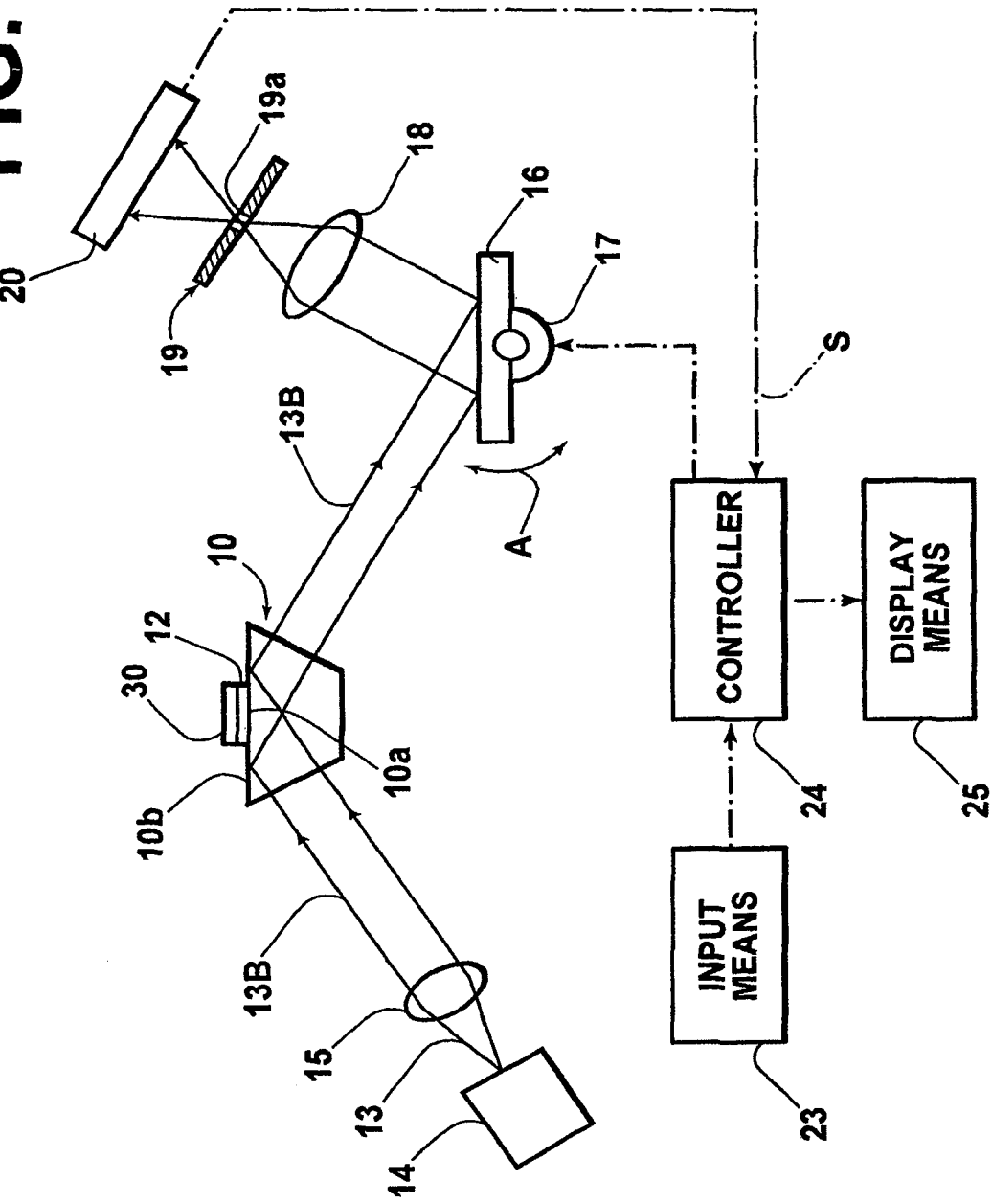
FIG. 10 is a schematic side view illustrating a leaky mode measurement apparatus according to a seventh embodiment of the present invention.

Next, a seventh embodiment of the present invention will be described. FIG. 10 illustrates a side view of a measurement apparatus according to the seventh embodiment of the present invention. The apparatus according to the seventh embodiment is, for example, a surface plasmon resonance measurement apparatus. The measurement apparatus in the present embodiment and the measurement apparatus illustrated in FIG. 1 are different from each other in that an input means 23, such as a keyboard, for inputting information is provided in the controller 24 in the present embodiment.

In the measurement apparatus of the present embodiment, an image including an image of the metal film 12 is displayed on the display means 25 based on the light detection signal S output from the CCD area sensor 20. An operator of the apparatus looks at the displayed image, and inputs information representing a standard point of the metal film 12 which has a predetermined rectangular pattern to the controller 24. The information representing the standard point of the metal film 12 is, for example, information representing the pixel position of each of four vertices of the metal film 12. Information such as that the standard points are, for example, vertices of a square of 1 cm×1 cm has been stored in the controller 24. The controller 24 corrects the light detection signal S output from the CCD area sensor 20 so that the pixel positions input by the operator become the vertices of the square stored in the controller 24. Accordingly, the positions on the metal film 12 and the positions on the light detection surface of the CCD area sensor 20 correspond to each other also in this case. Therefore, the distribution of the physical properties is displayed on the display means 25 so that the physical properties accurately correspond to the positions on the metal film 12.

The correction method according to the seventh embodiment, as described above, may be also applied to measurement apparatuses which are basically configured as described in the second through sixth embodiments of the present invention. When the correction method according to the seventh embodiment is applied to these measurement apparatuses, effects similar to the effect as described above may be achieved.

Figure 11:
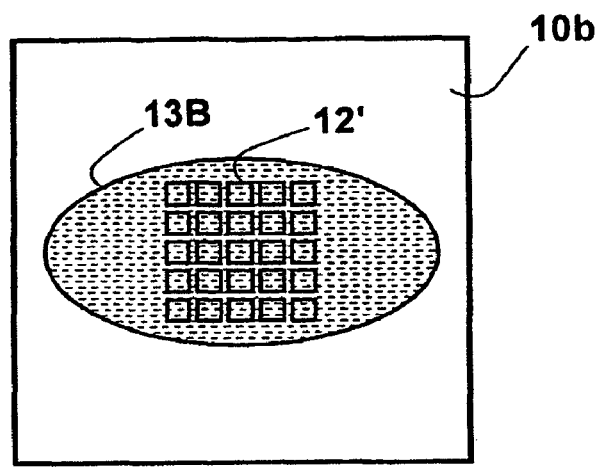
FIG. 11 is a plan view illustrating another example of a predetermined pattern in the present invention.

A predetermined pattern formed in the measurement apparatus according to the present invention is not limited to a rectangular pattern made of the metal film 12, as described above. The predetermined pattern may be made of a plurality of metal films 12' which are arranged cyclically, for example, as illustrated in FIG. 11.

Figure 12:
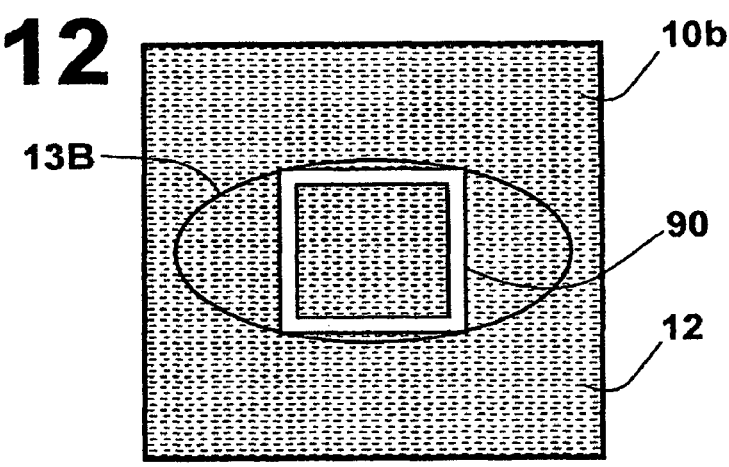
FIG. 12 is a plan view illustrating another example of a predetermined pattern in the present invention.

As illustrated in FIG. 12, the metal film 12 may be formed on the entire upper surface 10b of the dielectric block 10. Then, a predetermined pattern 90 made of a material which has a refractive index different from that of the sample, which is an analysis object, may be formed on the metal film 12. More specifically, the metal film 12 may be formed so that it has a uniform thickness of 50 nm, for example. Further, a predetermined pattern 90 which is made of a thin film of $SiO_2$, and which has a thickness of 1 nm, may be formed within a region irradiated with the light beam 13B on the metal film 12. The reflection properties of the pattern 90 as described above are different from those of the area surrounding the pattern 90. Therefore, if a reflected image is detected by the light detection means, the outline of the pattern can be easily discriminated. Please note that the material which has a refractive index different from that of the sample, as described above, is not limited to the thin film of $SiO_2$. The pattern may be also formed by a relatively thick metal film. The pattern made of the material as described above may be formed so that they are arranged cyclically as illustrated in FIG. 11.

Figure 13:
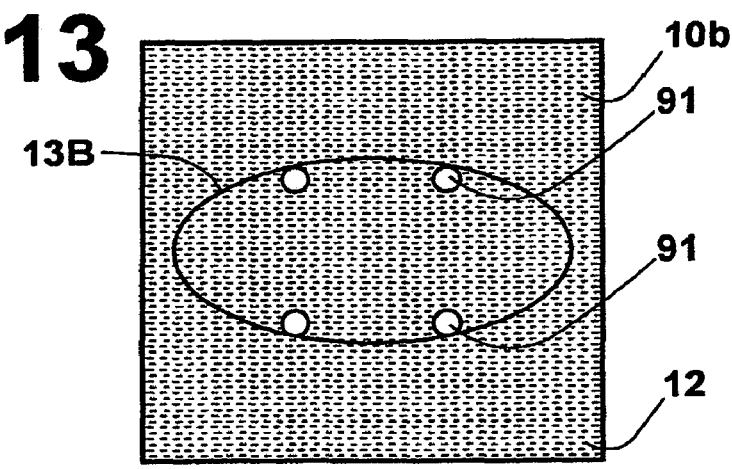
FIG. 13 is a plan view illustrating another example of a predetermined pattern in the present invention.

Further, when the metal film 12 is formed on the entire upper surface 10b of the dielectric block, a dot-shaped concavity 91 may be formed in the region of the metal film 12, as illustrated in FIG. 13. The dot-shaped concavity 91 may be used as the predetermined pattern. The total reflection and diffracted reflection as described above do not occur in a part of the upper surface 10b, at which the concavity 91 is formed, and the reflectance drops. Therefore, the position of the concavity 91 can be easily detected. It is preferable that the concavity 91 as described above is formed, for example, at a vertex of a rectangle to detect a position on the measurement plane.

Further, the concavity as described above may be a groove which forms a linear or rectangular pattern. Further, a plurality of dot-shaped or linearly-shaped concavities may be formed and arranged cyclically.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A measurement apparatus comprising:
   a dielectric block;
   a thin film layer which is formed on a face of the dielectric block and brought into contact with a sample, and which has a refractive index lower than that of the dielectric block;

a light source for generating a light beam;

an incident optical system for causing the light beam to enter the dielectric block so that total reflection conditions are satisfied at the interface between the dielectric block and the thin film layer;

a two-dimensional light detection means for measuring the intensity of the light beam totally reflected at the interface at each of a plurality of positions on the cross-section of the beam; and a correction means, wherein a predetermined pattern having a predetermined shape is formed within a region irradiated with the light beam on the face of the dielectric block, and wherein the correction means is a means for correcting an output from the two-dimensional light detection means, based on the predetermined shape of the pattern, so that the shape of an object on the face of the dielectric block and the shape of the object, detected by the two-dimensional light detection means, are similar to each other, wherein the correction means matches the output from the two-dimensional light detections means with the predetermined shape of the pattern as a basis for the correction.

2. A measurement apparatus as defined in claim 1, wherein the predetermined pattern is produced by forming the thin film layer into the predetermined pattern.

3. A measurement apparatus as defined in claim 1, wherein the predetermined pattern is produced by forming a material having a refractive index different from that of the sample into the predetermined pattern.

4. A measurement apparatus as defined in claim 1, wherein the predetermined pattern is a concavity formed on the face of the dielectric block.

5. A measurement apparatus as defined in claim 4, wherein total reflection and diffracted reflection do not occur at which the concavity is formed.

6. A measurement apparatus as defined in claim 4, wherein the concavity is arranged at a position of each vertex of a rectangle.

7. A measurement apparatus as defined in claim 4, wherein the concavity is arranged cyclically.

8. A measurement apparatus as defined in claim 1, wherein the output from the two-dimensional light detection means is input to the correction means, and the output from the two-dimensional light detection means is a light detection signal generated by the two-dimensional light detection means.

9. A measurement apparatus as defined in claim 1, wherein the correction means obtains physical properties of the sample based on the output from the two-dimensional light detection means.

10. A measurement apparatus as defined in claim 1, wherein a reflected image is obtained of an upper surface of the dielectric block from a position directly above the thin film layer, such that the correction means detects a position at which a density value changes stepwise in an image of the metal film layer to obtain an outline image of the predetermined shape of the thin film layer to be stored as a template.

11. A measurement apparatus as defined in claim 10, wherein the correction means performs template matching by gradually inclining the template such that the template and an outline image of the output from the two-dimensional light detection means match each other, and wherein the predetermined shape of the template and the shape of the object detected by the two-dimensional light detection means are similar to each other.

12. A measurement apparatus as defined in claim 11, wherein the correction means obtains an inclination of the outline image of the output of the two-dimensional light detection means based on the inclination of the template when the template and the outline image of the output match each other, and the correction means corrects the output from the two-dimensional light detection means so that the inclination of the outline image of the output is adjusted.

13. A measurement apparatus as defined in claim 1, wherein the predetermined shape of the predetermined pattern forms a template on the thin film layer to be referenced when the sample is analyzed for correction by the correction means.

14. A measurement apparatus comprising:

a dielectric block;

a diffraction grating formed on a face of the dielectric block;

a thin film layer which is formed on the diffraction grating and brought into contact with a sample;

a light source for generating a light beam;

an incident optical system for causing the light beam to enter the dielectric block so that at least a part of the diffraction grating is irradiated;

a two-dimensional light detection means for measuring the intensity of the light beam which has been reflectively diffracted at the diffraction grating at each of a plurality of positions on the cross-section of the beam; and a correction means, wherein a predetermined pattern having a predetermined shape is formed within a region irradiated with the light beam on the face of the dielectric block, and wherein the correction means is a means for correcting an output from the two-dimensional light detection means, based on the predetermined shape of the pattern, so that the shape of an object on the face of the dielectric block and the shape of the object, detected by the two-dimensional light detection means, are similar to each other, wherein the correction means matches the output from the two-dimensional light detections means with the predetermined shape of the pattern as a basis for the correction.

15. A measurement apparatus as defined in claim 14, wherein the predetermined pattern is produced by forming a material having a refractive index different from that of the sample into the predetermined pattern.

16. A measurement apparatus as defined in claim 14, wherein the predetermined pattern is a concavity formed on the face of the dielectric block.

17. A measurement apparatus as defined in claim 16, wherein total reflection and diffracted reflection do not occur at which the concavity is formed.

18. A measurement apparatus as defined in claim 14, wherein the correction means obtains physical properties of the sample based on the output from the two-dimensional light detection means.

19. A measurement apparatus as defined in claim 14, wherein a reflected image is obtained of an upper surface of the dielectric block from a position directly above the thin film layer, such that the correction means detects a position at which a density value changes stepwise in an image of the metal film layer to obtain an outline image of the predetermined shape of the thin film layer to be stored as a template.

20. A measurement apparatus as defined in claim 19, wherein the correction means performs template matching by gradually inclining the template such that the template and an outline image of the output from the two-dimensional light detection means match each other, and wherein the predetermined shape of the template and the shape of the object detected by the two-dimensional light detection means are similar to each other.

21. A measurement apparatus as defined in claim 20, wherein the correction means obtains an inclination of the outline image of the output of the two-dimensional light detection means based on the inclination of the template when the template and the outline image of the output match each other, and the correction means corrects the output from the two-dimensional light detection means so that the inclination of the outline image of the output is adjusted.

* * * * *